United States Patent
Shaw

[19]

[11] Patent Number: 6,015,438
[45] Date of Patent: Jan. 18, 2000

[54] FULL DISPLACEMENT RETRACTABLE SYRINGE

[75] Inventor: Thomas J. Shaw, Little Elm, Tex.

[73] Assignee: Retractable Technologies Inc., Little Elm, Tex.

[21] Appl. No.: 08/970,828

[22] Filed: Nov. 14, 1997

[51] Int. Cl.⁷ .................................................. A61M 5/00
[52] U.S. Cl. ........................................ 624/195; 604/110
[58] Field of Search .................... 604/110, 192, 604/195, 198, 214, 226

[56] References Cited

U.S. PATENT DOCUMENTS

| | | |
|---|---|---|
| 4,838,863 | 6/1989 | Allard et al. . |
| 4,838,869 | 6/1989 | Allard . |
| 4,874,382 | 10/1989 | Lindemann et al. . |
| 4,927,414 | 5/1990 | Kulli . |
| 4,994,034 | 2/1991 | Botich et al. . |
| 5,019,044 | 5/1991 | Tsao . |
| 5,049,133 | 9/1991 | Pascual . |
| 5,053,010 | 10/1991 | McGary et al. ........................ 604/110 |
| 5,084,018 | 1/1992 | Tsao . |
| 5,114,410 | 5/1992 | Batlle . |
| 5,180,369 | 1/1993 | Dysarz . |
| 5,188,599 | 2/1993 | Botich et al. . |
| 5,201,710 | 4/1993 | Caselli . |
| 5,211,629 | 5/1993 | Pressly et al. . |
| 5,304,138 | 4/1994 | Mercado . |
| 5,370,620 | 12/1994 | Shonfeld . |
| 5,385,551 | 1/1995 | Shaw . |
| 5,389,076 | 2/1995 | Shaw . |
| 5,407,431 | 4/1995 | Botich et al. . |
| 5,423,758 | 6/1995 | Shaw . |
| 5,578,011 | 11/1996 | Shaw ...................................... 604/110 |
| 5,613,952 | 3/1997 | Pressly, Sr. et al. . |

Primary Examiner—Wynn Wood Coggins
Assistant Examiner—A. T. Nguyen
Attorney, Agent, or Firm—Locke Liddell & Sapp LLP

[57] ABSTRACT

A full displacement retractable syringe has a front mounted retraction mechanism and a plunger with a sliding seal and a retraction opening with a sliding stopper. A needle holder is held in place with a holding ring which seals the front part of the barrel from fluid leakage and forms the bottom of a variable chamber in the barrel. The top of the variable chamber is formed by the nose of the plunger with its sliding plunger seal and stopper. Substantially all of the fluid contained in the variable chamber is expelled through a needle when the plunger is depressed to bring the upper and lower boundaries of the fluid chamber together. Because the plunger seal is restrained from forward movement by a stop in the barrel, the nose of the plunger slides through the plunger seal to operate the retraction mechanism. When the holding ring and stopper are gradually removed an instable state is reached whereby a spring compressed under the head of the needle holder overcomes remaining holding forces and the needle holder and needle together with the stopper are forced rearwardly into the retraction cavity. The syringe can be reused only until the plunger is fully depressed after the last injection. Coincident with the retraction action, the plunger enters the barrel to prevent reuse.

19 Claims, 4 Drawing Sheets

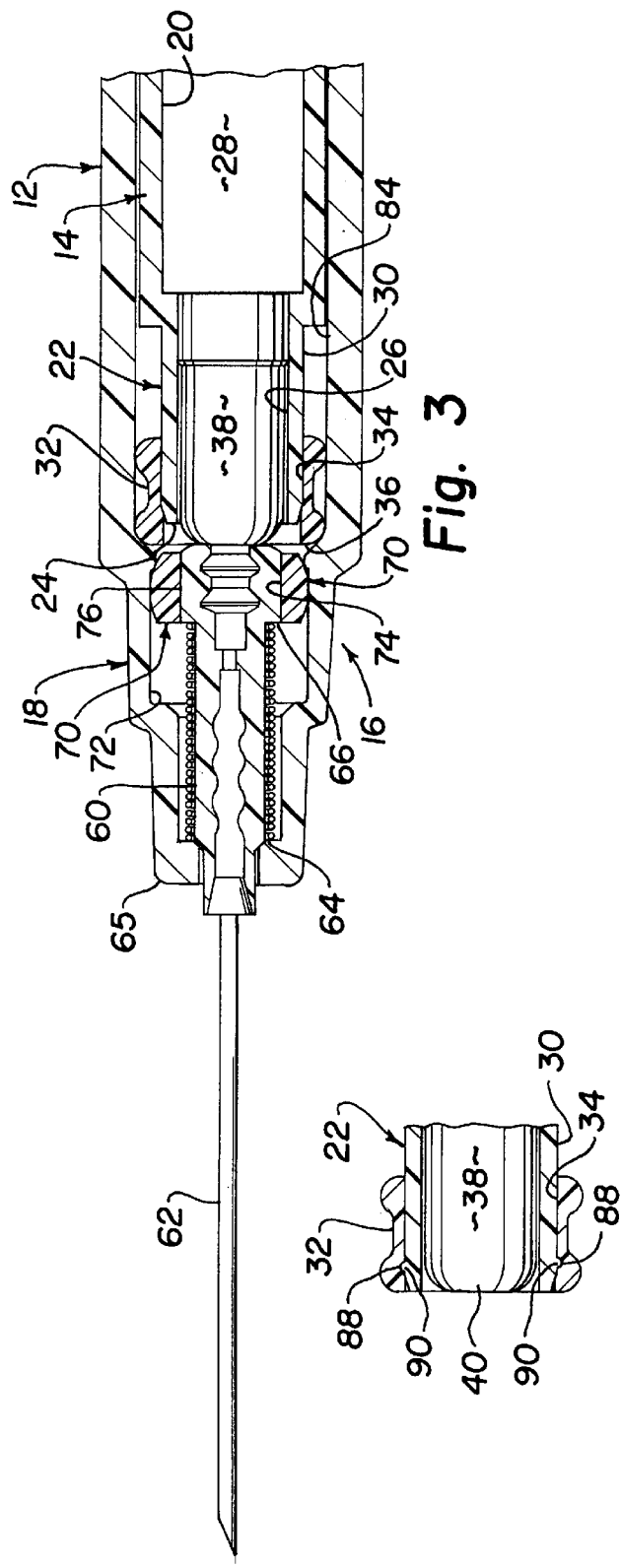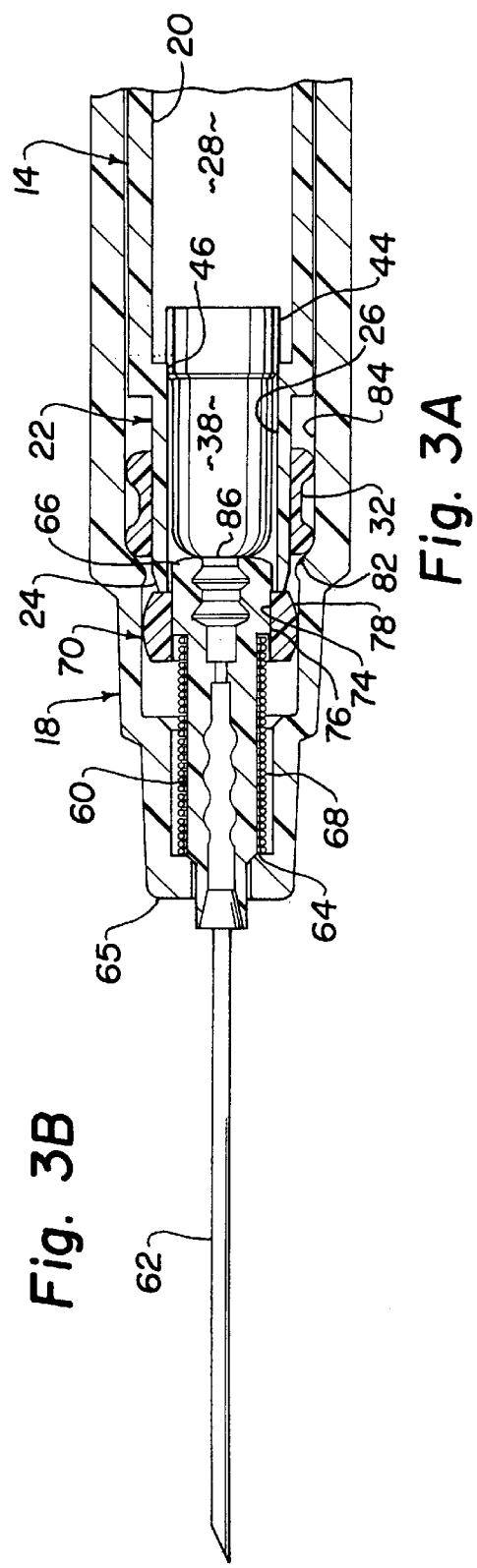
Fig. 3
Fig. 3A
Fig. 3B

FULL DISPLACEMENT RETRACTABLE SYRINGE

BACKGROUND OF THE ART

1. Field of the Invention

The invention pertains to medical devices for fluids, more particularly syringes with a retraction feature.

2. Background of the Prior Art

The syringe art has advanced rapidly in recent years because of the threat of AIDS and other infectious diseases and the inevitability of accidental needle sticks suffered by healthcare providers from the use of needles on infected patients. Used syringes with extended needles present a risk to medical personnel and sanitation employees and other in the disposal chain.

Most of the prior art retractable syringes are theoretical devices only which have never reached the market because of various practical deficiencies. These practical deficiencies relate to complexity, reliability, repeatability, cost and ease of use. Syringes must be mass produced at the rate of millions per day. Cost is a significant factor in manufacture of the parts and the assembly of the device. Automated production of parts and assembly of parts is critical in order to have any hope of supplying a practical syringe to the market. A significantly improved retractable syringe is disclosed in my U.S. Pat. No. 5,385,551, the disclosure of which is incorporated herein by reference.

In a curious development, healthcare workers in the drug control field have expressed a need for a reusable retractable syringe to prevent the spread of AIDS. Such a syringe is preferably a full displacement syringe which will deliver essentially all of the contents without retracting and without limiting the ability of the user to draw a second dose. Hopefully the drug user will confine use to himself without sharing the needle but can retract the needle when finished and render the device inoperable.

There is also a need for a multiple use retractable syringe for diabetics to use at home to inject insulin, where AIDS is not a factor. After a day's use, for instance, the home user can retract the syringe to prevent any risk to others in the disposal chain. All this is to be accomplished without affecting the ability of professional healthcare workers from injecting a dose into a patient and then initiating retraction and non-reusability while the needle is still in the patient's arm. In all embodiments, retraction renders the syringe non-reusable. The present invention is designed to accomplish these goals and more.

SUMMARY OF THE INVENTION

A retractable full displacement syringe is provided which is reusable only until the plunger is finally depressed fully after the last injection. The syringe has an elongated housing comprising a hollow barrel having a front end portion with a wall defining an inner surface and an opening at the back of the barrel calculated to closely receive the thumb cap of the plunger to prevent reuse after retraction. The plunger has a nose portion in front and a forcibly slidable plunger seal mounted on and around the nose at the front of the nose which moves with the plunger during normal syringe operations. A slidable removable stopper seals a retraction opening within the nose of the plunger.

There is a retraction mechanism mounted in the front part of the barrel characterized by an elongated needle holder having a reduced diameter front end portion and a generally straight body section circumscribed by a compressed spring and an enlarged head behind which is slidably and preferably frictionally held in the front end portion by a movable holding ring member which traverses the barrel to the interior surface of the wall thereby holding the retraction mechanism in place and forming the bottom and lower boundary of a variable fluid chamber in the barrel. A needle is attached to the needle holder in fluid communication with the variable chamber through an opening maintained in the needle holder.

A stop in the barrel interiorially prevents forward movement of the plunger seal after it reaches the bottom of the variable fluid chamber. The generally evenly aligned tip of the nose, front of the stopper and the plunger seal, form the upper boundary of the variable fluid chamber. The leading wall portion of the nose of the plunger has a removably sealed opening large enough to receive the head of the needle holder while pressing against the movable holding ring member.

Depression of the plunger brings the effective piston formed by the plunger seal, nose and stopper against the bottom of the variable fluid chamber thereby expelling substantially all fluid from the chamber. Further depression of the plunger causes the plunger nose to slide forward through the plunger seal and causes the leading wall of the tubular nose of the plunger to operate the retraction mechanism by moving through the plunger seal to push the movable holding ring off the head of the needle holder, thereby initiating retraction. The dislodgable stopper in the opening of the tubular nose which slidingly seals the retraction cavity is forced to slide back as the plunger moves forward relative to the head of the needle holder.

The parts for this improved syringe are relatively few and well suited for mass production and automated assembly. The holding ring and plunger seal are symmetrical so that they can be assembled in either of two orientations. The sliding plunger seal makes it possible to expel substantially all fluid and still allow additional forward plunger movement necessary to operate the retraction mechanism and bury the back end of the plunger within the barrel opening to prevent subsequent access to the now disconnected interval parts.

Fail safe operation can be provided by configuring the slidable parts so that the plunger seal is the first to move in preference to the holding ring or stopper in the event excessive force is employed during an injection. Such movement is not a failure mode and does not results in any leak of fluid.

BRIEF DESCRIPTION OF THE DRAWINGS

FIG. 3 is an enlarged view of the front end portion of the barrel and the plunger of FIG. 2;

FIG. 3A shows the embodiment of FIG. 3 upon further depression of the plunger whereby the plunger moves through the plunger seal to initiate retraction just before the needle holder is released;

FIG. 3B illustrates an alternate way of keeping the plunger seal from sliding in response to longitudinally directed shifting force;

DETAILED DESCRIPTION OF THE INVENTION

Figure 1:
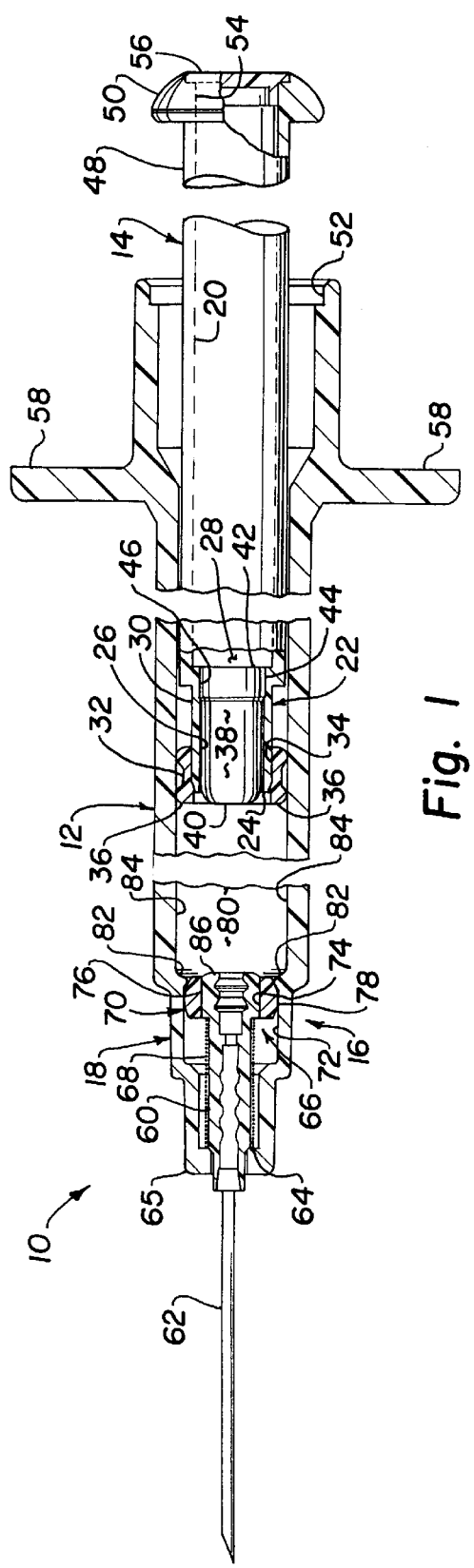
FIG. 1 is a partially cut away side view of one embodiment of the invention showing the sliding plunger seal and stopper selectively positioned partly forward with respect to the plunger nose.

In the description that follows, like parts will be referred to by the same reference numeral. The full displacement syringe in FIG. 1 is referred to generally by the reference numeral 10. The combination includes an elongated housing 12 which is often referred to as a barrel. A plunger 14 is configured to reciprocate in barrel 12. A retraction mechanism 16 is mounted in a front end portion 18 of barrel 12. As indicated in the drawings, the components and parts are generally tubular and circular.

Plunger 14 is an elongated tubular plunger having a wall 20 configured in front to have a reduced diameter tubular nose 22 in the form of a protruding tip. Nose 22 is formed as a leading wall portion extending forwardly from wall 20 and terminating in a protruding tip portion 24. Nose 22 has a removably sealed opening 26 leading into a retraction cavity 28 in plunger 14.

Tubular nose/protruding tip 22 has an outer bearing surface 30 for a slidable plunger seal 32. Plunger seal 32 is forcibly slideably mounted near the front of tubular nose 22 in a selected position. The shape of plunger seal 32 is generally cylindrical with a cylindrical inner bearing surface 34 in frictional sliding contact with bearing surface 30. Plunger seal 32 has a front end 36 and an overall length which is substantially less than the longitudinal length of bearing surface 30. The term "forcibly slidably" with respect to the plunger seal is meant to indicate that the plunger seal can slide longitudinally along tubular nose 22 upon application of a sufficient longitudinally directed shifting force. It also can mean that plunger seal 32 being preferably an elastomer has an inside opening 34 which is stretched to fit on the front end of nose 22 thereby being frictionally held in place until a sufficient longitudinal shifting force is employed to cause seal 32 to move relative to plunger 14.

Opening 26 in nose 22 is removably sealed by means of an elongated stopper 38 having a front end 40 and a rear end 42 with a slightly enlarged bearing or engagement surface 44 in sliding frictional engagement with an inner surface portion 46 of the inner surface of the opening 26 leading into retraction cavity 28. Inner surface 46 may be the same diameter or a different diameter than the inner surface of opening 26. Surfaces 44, 46 are engaging surfaces which slidingly engage to resist longitudinal shifting force applied to stopper 38 during normal syringe operations, but which allow the stopper to be pushed back into the retraction cavity during retraction of the needle.

Figure 4:
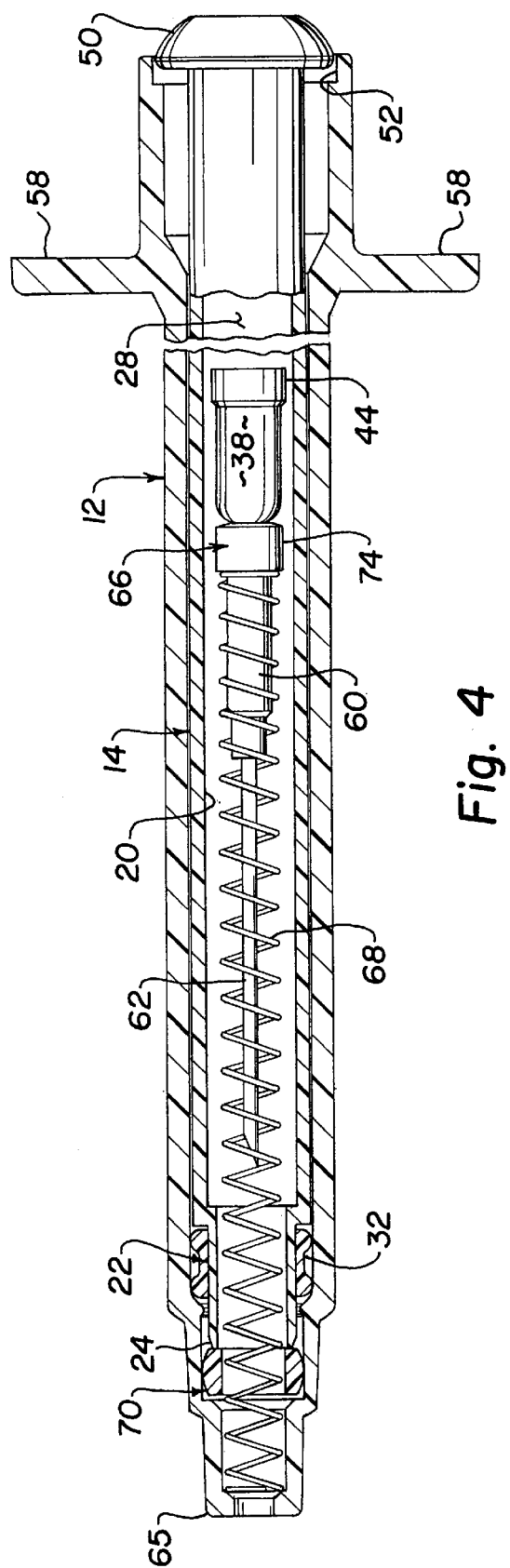
FIG. 4 shows retracted syringe of FIGS. 1–3 after complete depression of the plunger with the thumb cap inaccessibly positioned in an opening at the back of the barrel.

The back end portion 48 of plunger 14 includes a circular thumb cap 50 designed to fit closely within an opening 52 of barrel 12 when the plunger is fully depressed to the retracted position shown in FIG. 4. End portion 48 includes an opening 54 through which stopper 38 is conveniently inserted during assembly and a seat 56 for an end cap (not shown) which plugs opening 54 thereby preventing retraction components or fluid from exiting the syringe. Plunger 14 includes the usual finger grips 58 of any conventional construction.

Retraction mechanism 16 comprises an elongated needle holder 60 connected to a needle 62 with an opening therethrough. Needle holder 60 may include a stepped portion 64 which seats against the barrel at the front 66 of barrel 12. Needle holder 60 has a head 66 which is larger than its body. A biasing element comprising spring 68 circumscribes the body of needle holder 60 in a compressed state under head 66. A movable holding ring 70 is slidably mounted on the head of the needle holder. Holding ring 70 extends laterally to contact and slidably engage the inner wall surface 72 of the front end portion 18 of barrel 12. Holding ring 70 has an inner surface 74 in sliding preferably frictional engagement with an outer surface 76 of needle holder 60. The irregular internal openings in needle holder 60 are designed to hold adhesive for needle 62.

Space is provided below holding ring 70 to allow ring 70 to be moved forward off head 66 thereby freeing the needle holder and needle to retract. Holding ring 70 has an outer surface 78 in slidable contact with inner surface 72. Ring 70 extends transversely to close the opening and hold the spring loaded needle holder 60 in the unretracted position shown in FIG. 1. The retraction mechanism, comprising head 66 of the needle holder and holding ring 70, form the bottom of a variable fluid chamber 80 formed in the barrel below the piston formed by the nose of the plunger together with the plunger seal and stopper. The plunger nose, plunger seal and stopper form the upper boundary of variable chamber 80.

A plunger seal restraint 82 is located on the barrel wall to restrain the plunger seal from forward movement after it has reached the bottom of variable chamber 80. Plunger seal restraint 82 preferably takes the form of an annular reduction in diameter in the nature of an inwardly raised portion of the barrel wall. Restraint 82 may extend inwardly beyond inner wall 84 of barrel 12 as well beyond inner wall surface 72 below holding ring 70. Seal restraint 82 serves as a stop in the barrel which prevents forward movement of the plunger seal after it reaches the bottom of the variable fluid chamber 80 thereby expelling substantially all fluid. Although restraint 82 is shown as a molded in intrusion from the wall of barrel 12, it can be appreciated that plunger seal restraint 82 could be a separate part configured to restrain plunger seal 32 from forward movement after it reaches the bottom of variable chamber 80 without preventing plunger nose 22 from sliding forward through the plunger seal to operate retraction mechanism 16.

Figure 2:
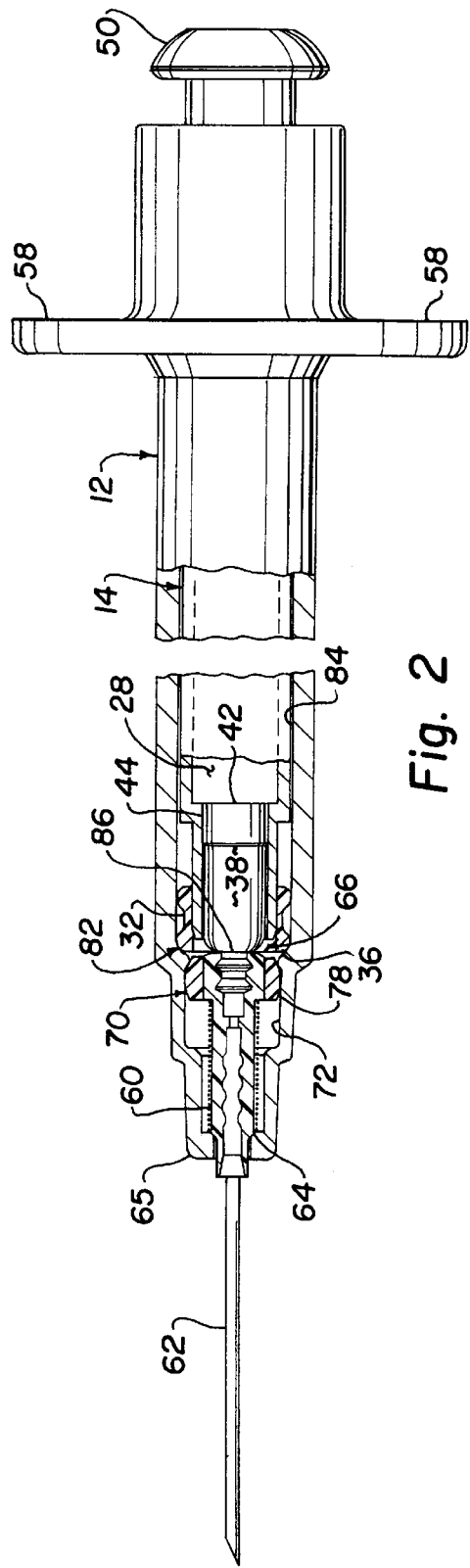
FIG. 2 shows the partially cut away side view of FIG. 1 after the plunger has been depressed to end an injection cycle with the plunger seal restrained from further forward movement by the barrel of the plunger and the stopper in position to be dislodged by further depression of the plunger toward the holding ring.

FIGS. 2 and 3 illustrate the full displacement syringe of FIG. 1 after fluid has been drawn into variable chamber 80 by partially withdrawing plunger 14 and then dispensing the fluid through needle 62 by depression of the plunger. This fully collapses variable chamber 80 by bringing the lower boundary of the variable chamber formed by retraction mechanism 16 and the upper boundary of the variable chamber together. In FIGS. 2 and 3, the front 36 of plunger seal 38 has been fully restrained and stopped from further movement by restraint 82. Front 40 of stopper 38 is contacting back 86 of the head of needle holder 60. Needle holder 60 is fixed in place and cannot move forward because its forward end is grounded in the front 65 of barrel 12. It can be seen that only a very small amount of undisplaced fluid can be present at this stage of the operation. Further depression of the plunger causes the nose 22 to slide through the center of plunger seal 32 and causes the stopper to slide rearward relative to the plunger. These sliding processes continue as the plunger slides forward. It is preferred that the front of nose 22 be "castled" with short gaps to prevent fluid from being trapped when the tip 24 reaches holding ring 70.

FIG. 3A represents the condition of FIGS. 2 and 3 upon further depression of the plunger showing that the protruding tip portion 24 of nose 22 of plunger 14 is pushing holding ring 70 from the head 66 of needle holder 60. It can be seen that the amount of remaining portions of engaging surfaces 74, 76 has been significantly reduced as holding ring 70 is moved forward and a similar disengagement has occurred with respect to the amount of remaining engagement of surfaces 44, 46 between opening 26 in nose 22 and stopper 38. Thus the stage is set for immediate retraction.

FIG. 4 shows the full depression of the plunger and complete retraction. Holding ring 70 has been pushed forward off head 66 of needle holder 60 thereby releasing the needle holder from restraint. Spring 68 pressing rearwardly under head 66 of needle holder 60 drives the needle holder and removes any remaining portion of the stoppers engagement to drive them back into retraction cavity 28. It can be seen that plunger seal 32 has been moved from what may be considered a first position in FIGS. 1–3 to a second position behind the first position by about the width of seal member 32.

Figure 5:
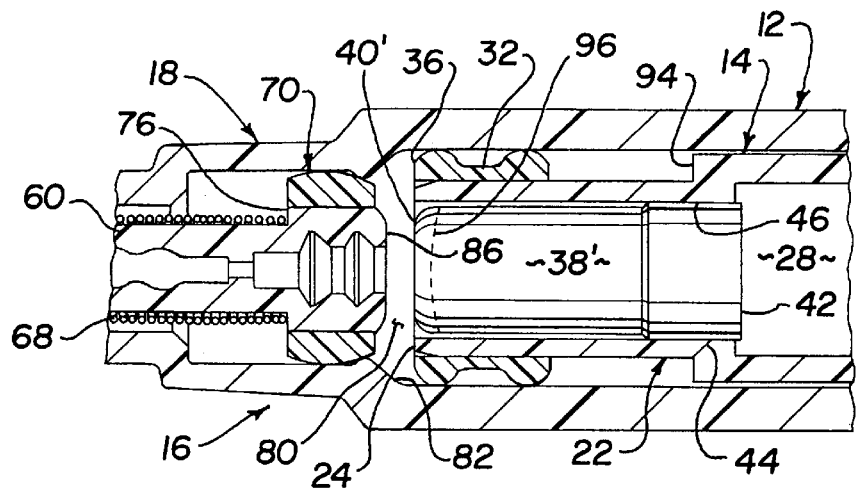
FIG. 5 illustrates an alternate selected position of the plunger seal and stopper to optimize the full displacement feature and to provide sequential overcoming of static friction as retraction is triggered by depression of the plunger.
Figure 6:
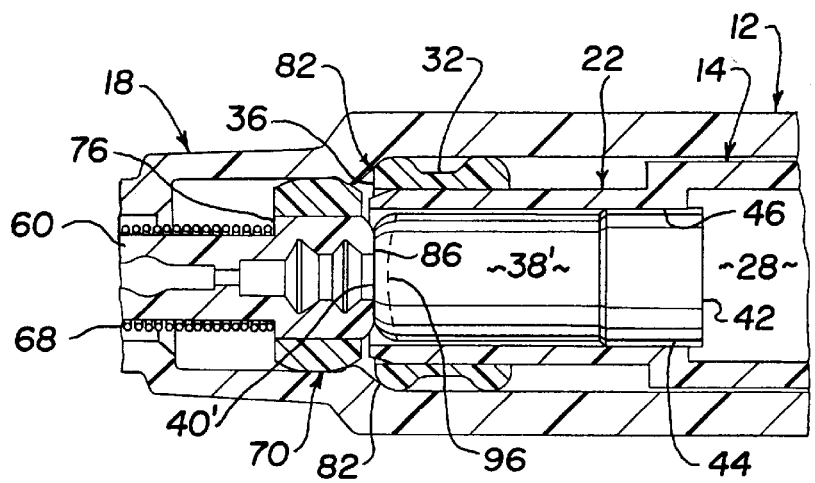
FIG. 6 is the arrangement of FIG. 5 as the plunger seal reaches the bottom of the variable fluid chamber in the barrel at the end of an injection stroke.

FIGS. 5 and 6 illustrate the optimum full displacement syringe of FIGS. 1–4 achieved by selective positioning of plunger seal member 32's front 36 flush with tip 24 of nose 22. In addition, slidable stopper 38' has a modified front 40' as compared to the structure of FIGS. 1–4 which lines up flush with front 36 and tip 24.

FIG. 6 shows the structure of FIG. 5 slightly after the end of an injection cycle whereby nearly full displacement of any remaining fluid in variable chamber 80 has been achieved. When it is recognized that the preferred form of this syringe is a 1 cc version where the barrel has a width of approximately 0.63 centimeters, one can appreciate just how small the amount of remaining fluid in collapsed variable chamber 80 really is. It also illustrates a preferred sequence of sliding movements to create a smooth triggering force as the plunger is depressed for retraction.

The selected positioning of the slidable plunger seal, stopper and holding ring avoid cumulation of static friction triggering forces on the plunger which must be overcome during retraction. As indicated in FIG. 6, once the piston which is the combination of the plunger seal, nose and stopper bottoms out, it bottoms out in a sequential way. First plunger seal 32 is stopped by restraint 82 allowing plunger 14 to start sliding through the center of seal 32. This continues as next, front 40' of stopper 38' is stopped by the back surface 86 of head 66 of needle holder 60. Plunger nose 22 continues moving forward a short distance before then encountering the back surface of holding ring 70 which begins moving forward relative to head 66 of needle holder 60. This configuration has the benefit of sequentially overcoming static friction respectively of the plunger seal, stopper and holding ring.

An alternate sequence of creating sequential dynamic movement of the sliding parts is represented by the dotted line 96 in FIGS. 5 and 6 which represents the front of a shortened stopper 38, 38'. This same position could be obtained with the same stopper by lengthening the back of the nose or shortening the land 44 which engages opening 26. In this sequence of operations, depression of the plunger first causes dynamic motion of the plunger seal relative to the moving plunger as the seal reaches stop 82 or its equivalent. Secondly, tip 24 engages holding ring 70 and begins dynamic movement relative to the head of the stationary needle holder before the front 96 (dotted line) of stopper 38, 38' contacts the head of the needle holder. Thirdly, dynamic motion of the stopper relative to the plunger is initiated while the first and second dynamic sliding motions are continued.

Figure 7:
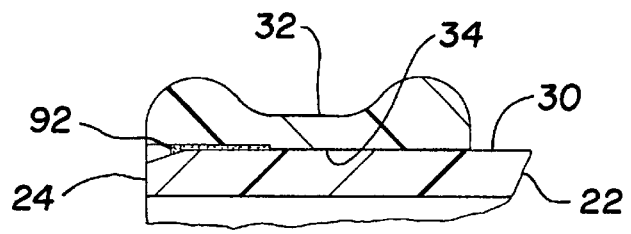
FIG. 7 shows an alternate way of holding the plunger seal on the end of the plunger by means of a bridging portion designed to allow the plunger seal to break free and slide in response to longitudinally directed shifting force.

FIG. 3B and FIG. 7 illustrate several ways of providing resistance against longitudinal shifting force which may result from hydraulic pressure force in the variable chamber generated during an injection. Similar methods may also be used to resist or help resist shifting forces applied to the stopper or the ring member. In FIG. 3B preferably at the forward end of the nose 22, an annular ring or plurality of ring segments or the like 88 may be formed as a slight enlargement of the surface 30 on the nose. A corresponding depression 90 may be formed around the inside surface 34 of plunger seal 32. When front 36 of seal 32 reaches a restraint 82 in the wall, plunger 14 continues moving. The interlocking raised portion 88 and the corresponding depression 90 must be disengaged forcibly before plunger seal 32 is free to slide on nose 22.

FIG. 7 illustrates that it may be possible to introduce a bridge or bridges of material 92 between the inner surface of seal 32 and the outer surface 30 of nose 22. These bridges can be one or more adhesive stripes or spots or hot melts or even tiny welded areas which may be formed by ultrasonic welding if the materials are plastics that are weldable. Such a bridge of material can provide a frictional hold or part of the frictional resistance to shifting force which allows the plunger or other sliding part to break free in response to a desired longitudinal shifting force.

In the best mode, the syringe is preferably made with a one piece barrel as best shown in FIG. 4. Assembly of the retraction mechanism is from the rear of the barrel. The stopper is preferably loaded through the opening in back of the plunger which is preferably sealed after the stopper is lodged in the opening of the nose. The barrel diameter and cross section of the holding ring, plunger seal and stopper and the frictional force required to shift them are selected in substantial balance with each other so that hydraulic pressure will not cause a blow out prematurely during an injection. A blow out is considered to be an undesirable premature shifting or complete release of a slidable part in response to the force generated in the variable chamber due to pressure resulting from depression of the plunger during an injection.

It is expected that the relative cross sectional areas of the plunger seal, holding ring and stopper and the force required to shift them should be selected to withstand a plunger depression force of about 6 to 10 pounds force without shifting. Generally it is desirable to have a relatively thin plunger seal, otherwise the hydraulic pressure induced force may be so great as to slide the plunger seal back on the nose in response to a vigorous injection. The area of the plunger seal exposed to such force and the frictional resistance to sliding is preferably selected so that excessive hydraulic force will tend to move the plunger seal before moving the holding ring or stopper to effectual fail safe operation. If the stopper or the holding ring blow out first, it is a failure of the device. If the plunger seal moves back because of excessive force produced by hydraulic pressure, there is no retraction and no escape of fluid from the device. All that happens is additional space is provided for fluid which tends to mitigate the effect of the high pressure. Since the seal can only slide back until it hits the back 94 of nose 22, little damage is done. Of course, it is undesirable to have this happen because it will tend to reduce slightly the size of dose injected.

If we assume that the frictional holding force of the slidable parts, namely the plunger seal, stopper and holding ring are equal, then it is a matter of calculation to balance the cross sectional area of each of these three parts which is exposed to hydraulic pressure. Limiting factors are that the head of the needle holder must be able to fit inside and traverse the opening in the nose of the plunger to reach the retraction cavity. Another limiting factor is that the tip of the nose must be able to pass through the reduced diameter area where the plunger restraint or stop is located in the barrel. At the same time it must directly reach the holding ring in order to push it from the head of the needle holder. The holding force on these three sliding parts to resist shifting is preferably frictional force arising from stress. Stress may be generated by an interference fit. The triggering force necessary to cause retraction is expected to be any force above the estimated operating range of about 6 to 10 pounds of plunger force.

Although the present invention has been described in detail with reference to only the presently preferred embodiments, it will be appreciated by those of ordinary skill in the art that various modifications can be made without departing from the invention.

I claim:

1. A full displacement syringe, comprising:
    an elongated housing comprising a hollow barrel having a front end portion, and an inner surface;
    a plunger configured to reciprocate in the barrel, the plunger having a retraction cavity within and a tubular nose in front with a leading wall having a removably sealed opening into the retraction cavity;
    a retraction mechanism mounted in the front end portion of the barrel, the retraction mechanism comprising a needle and needle holder having a head, a biasing element tending to drive the needle holder rearwardly and a movable holding ring mounted on the head of the needle holder, said ring holding the retraction mechanism by contact with the inner surface of the barrel, wherein the retraction mechanism forms the bottom of a variable fluid chamber in the barrel;
    a plunger seal forcibly slideably mounted near the front of the tubular nose of the plunger, said plunger seal being movable with the plunger in sliding contact with the inner surface of the barrel during fluid transfer operations;
    a plunger seal restraint located on the barrel wall to restrain the plunger seal from forward movement after it has reached the bottom of the variable chamber without said restraint preventing the plunger nose from sliding forward through the plunger seal to operate the retraction mechanism;
    whereby depression of the plunger to place the plunger seal at the bottom of the variable fluid chamber causes substantially full displacement of fluid from the barrel and further forward movement of the plunger causes the leading wall of the tubular nose of the plunger to operate the retraction mechanism by moving through the plunger seal to push the movable holding ring off the head of the needle holder, thereby initiating retraction.

2. The full displacement syringe of claim 1 wherein the removably sealed opening of the tubular nose of the plunger contains a dislodgable stopper which slidingly seals the retraction cavity.

3. The full displacement syringe of claim 2 wherein the plunger seal is positioned on the tubular nose to reach the restraint at the bottom of the variable chamber before the plunger nose begins pushing the holding ring off the head of the needle holder, thereby creating dynamic relative motion between the plunger and plunger seal before static friction between the holding ring and needle holder must be overcome.

4. The full displacement syringe of claim 3 wherein the relative positioning of the stopper and the plunger seal results in dynamic relative motion of the stopper with respect to the plunger in addition to the plunger seal before the tubular nose in front of the plunger begins releasing the holding ring from the needle holder.

5. The full displacement syringe of claim 3 wherein the relative positioning of stopper and the plunger seal with respect to the tubular nose would result in dynamic relative motion of the holding ring in addition to the plunger seal before the front of the stopper and needle holder could come together to cause dynamic motion of the stopper relative to the plunger.

6. The full displacement syringe of claim 4 wherein the needle holder has a step which seats against the barrel to prevent the needle holder from moving forward.

7. The full displacement syringe of claim 6 wherein the plunger includes a cap and the housing has a seat which closely receives the cap when the plunger moves forward as retraction is completed.

8. The full displacement syringe of claim 1 wherein said forcibly slidable plunger seal is forcibly slidably held on the tubular nose by friction sufficient to hold the plunger seal in place while drawing fluid into or expelling fluid from the variable chamber but insufficient to prevent relative sliding movement of the plunger through the plunger seal after the plunger seal engages the plunger seal restraint at the bottom of the chamber.

9. The full displacement syringe of claim 8 wherein said friction is provided at least in part by a bridge of material between the plunger seal and tubular nose which allows the plunger to break free from the plunger seal when the plunger seal is pushed against the restraint by depression of the plunger.

10. The full displacement syringe of claim 8 wherein said friction is provided additionally in part by one or more irregular surfaces on the tubular nose which hinder movement of the plunger seal until a threshold force is applied to the plunger seal by the plunger in combination with the restraint at the bottom of the variable chamber.

11. A full displacement syringe, comprising:
    a syringe barrel having a wall defining a hollow interior surface and a front end portion;
    a plunger having a nose portion in front and a forcibly slidable plunger seal on the nose that moves with the plunger during normal syringe operations;
    a retraction mechanism having a spring mounted in the front part of the barrel, characterized by a needle holder having a movable holding ring member which traverses the barrel to the interior surface thereof to hold the retraction mechanism in place above the compressed spring located under the needle holder, said retraction mechanism forming the bottom of a variable fluid chamber in the barrel;
    a stop in the barrel which prevents forward movement of the plunger seal after it reaches the bottom of the variable fluid chamber thereby expelling substantially all fluid;
    said nose portion of the plunger having a leading wall portion forming a removably sealed opening large enough to receive the head of the needle holder while pressing against said movable holding ring member;

whereby said plunger can move forward relative to said plunger seal after the plunger seal is at the bottom of the variable fluid chamber thereby causing said leading wall to dislodge and move said holding ring member off the head of the needle holder to initiate retraction.

12. The full displacement syringe of claim 11 wherein said removably sealed opening in the nose portion of the plunger is removably sealed with a stopper which is slidingly removed upon contact with the needle holder as the plunger moves forward.

13. The full displacement syringe of claim 12 wherein the barrel diameter and cross sectional area of the holding ring, plunger seal and stopper and the frictional force required to shift them, which is exposed to hydraulic pressure resulting from depression of the plunger, are selected in substantial balance with each other so that said pressure will not cause a blowout prematurely during an injection.

14. The full displacement syringe of claim 13 wherein the force resulting from said hydraulic pressure required to shift the plunger seal is less than to the force required to shift the holding ring and stopper so that excessive hydraulic force will tend to move the plunger seal before the holding ring or stopper to effectuate fail safe operation.

15. The full displacement syringe of claim 14 wherein the plunger seal, stopper, head of the needle holder and holding ring are positioned so that full depression of the plunger first results in the plunger seal reaching the stop, then the stopper contacting the needle holder and finally the leading wall portion of the nose contacting the holding ring to avoid cumulation of triggering force to be overcome during retraction.

16. The full displacement syringe of claim 14 wherein the plunger seal, stopper, head of the needle holder and holding ring are positioned so that depression of the plunger would first result in the plunger seal reaching the stop and the plunger sliding forward relative to the plunger seal to cause sliding motion of the holding ring relative to the needle holder before the front of stopper reaches the needle holder and begins sliding in order to avoid accumulation of triggering forces to be overcome during retraction.

17. The full displacement syringe of claim 13 wherein the relative cross sectional areas of the plunger seal, holding ring and stopper and the force required to shift them are selected to withstand a plunger depression force of about 6 to 10 pounds force without shifting.

18. A full displacement retractable syringe, comprising:

an elongated syringe housing having a tubular wall, comprising a nose portion in front, an intermediate body section and an opening behind for receiving a plunger;

a retraction mechanism mounted in the nose portion of the housing, the retraction mechanism comprising a needle and a rearwardly biased needle holder having a head portion and a holding ring releaseably mounted on the head portion and extending in sealing contact with the wall of the housing which together form the lower boundary of a variable fluid chamber in the housing;

an elongated tubular plunger having a wall configured in front to form a protruding tip, the protruding tip having a bearing surface for a slidable plunger seal to be mounted thereon and an opening therein leading into the plunger, the opening being occupied by a stopper slidingly mounted in said opening;

a plunger seal mounted on a front part of the bearing surface on the protruding tip, for movement with the plunger in sliding sealing contact with the housing, the plunger seal being slidable rearwardly along said bearing surface in response to force applied to the seal in excess of operational force or pressure force generated in the course of drawing and expelling fluid to or from said fluid chamber, wherein said tip, said stopper and said seal define the upper boundary of a variable fluid chamber in the housing;

whereby nearly all fluid previously drawn into the variable fluid chamber is expelled through the needle when the upper and lower boundaries of the fluid chamber are brought together by depression of the plunger to a first position, and retraction occurs by movement of the plunger forward beyond the first position whereby the plunger seal is constrained against forward movement by a restriction causing the plunger seal to slide rearwardly relative to the protruding tip while the protruding tip engages and pushes the holding ring from the head of the needle holder to free the needle holder and allow it to retract into the plunger through the opening in said tip.

19. A full displacement retractable syringe, comprising:

an elongated tubular housing comprising a barrel having a wall with an inner surface defining a hollow space comprising a fluid chamber and an opening behind;

a plunger having a tubular wall configured to define a protruding tip portion in front having a tip and a hollow interior, the hollow interior comprising a retraction cavity, the plunger having a thumb cap behind and being adapted for reciprocating movement within said housing;

an opening in the tip portion of the plunger leading into the retraction cavity and slidingly sealed by a removable stopper;

a plunger seal movably mounted in a forward position near the front of the protruding tip portion of the plunger, for slidable movement relative to the plunger from the forward position on said tip portion to a rearward position on said tip portion behind said forward position, said plunger seal extending laterally in sliding sealed contact with the inner wall of said housing to form a seal on the plunger for drawing or expelling fluid from the housing;

a retraction mechanism mounted in the front of the housing, the retraction mechanism having a needle mounted in an inwardly biased needle holder having a head portion fitted with a holding ring releaseably mounted thereon, the ring extending laterally in sealing contact with the wall of the housing;

the protruding tip, stopper and plunger seal comprising the upper boundary of a variable fluid chamber in the housing;

the needle holder head and holding ring comprising the lower boundary of the variable fluid chamber in the housing;

whereby fluid is fully displaced from the variable chamber when the upper boundary and lower boundary are brought together by forward movement of the plunger to a first position of the plunger;

retraction occurring by further forward movement of the plunger to a second position beyond said first position whereby the holding ring is pushed forwardly relative to the head of the needle holder by the end of the protruding tip while the needle holder and plunger seal are held stationary by the housing as the plunger moves forward until the needle holder comes free from the holding ring to retract along with the stopper into the retraction cavity of the plunger.

* * * * *